(12) United States Patent
Nivestedt et al.

(10) Patent No.: US 7,492,866 B2
(45) Date of Patent: Feb. 17, 2009

(54) COLLISION DETECTING DEVICE AND METHOD

(75) Inventors: Håkan Nivestedt, Sollentuna (SE); Alain Minoz, Bromma (SE)

(73) Assignee: Elekta AB (Publ), Stockholm (SE)

( * ) Notice: Subject to any disclaimer, the term of this patent is extended or adjusted under 35 U.S.C. 154(b) by 135 days.

(21) Appl. No.: 11/628,873

(22) PCT Filed: Jun. 23, 2005

(86) PCT No.: PCT/SE2005/000991

§ 371 (c)(1),
(2), (4) Date: Feb. 7, 2007

(87) PCT Pub. No.: WO2006/001768

PCT Pub. Date: Jan. 5, 2006

(65) Prior Publication Data

US 2008/0089483 A1    Apr. 17, 2008

Related U.S. Application Data

(60) Provisional application No. 60/583,361, filed on Jun. 29, 2004.

(30) Foreign Application Priority Data

Jul. 1, 2004  (SE) .................................. 0401695

(51) Int. Cl.
*H05G 1/54*  (2006.01)

(52) U.S. Cl. ........................... 378/117; 378/91; 378/204
(58) Field of Classification Search ................... 378/65, 378/68, 69, 91, 95, 98, 117, 204, 205, 207–209
See application file for complete search history.

(56) References Cited

FOREIGN PATENT DOCUMENTS

| EP | 0 582 345 A1 | 2/1994 |
|---|---|---|
| GB | 2340716 A | 2/2000 |
| WO | WO 0059575 A1 | 10/2000 |

*Primary Examiner*—Jurie Yun
(74) *Attorney, Agent, or Firm*—Buchanan Ingersoll & Rooney PC

(57) ABSTRACT

The present invention relates to a collision detecting device for a radiation treatment apparatus, comprising a radiation unit having an internal space, for directing radiation beams towards a radiological focus in the internal space for treatment of a target in a patient's body therein. The collision detecting device comprises a collision detecting unit being electrically conductive at least on its outer surface and having a size slightly smaller than the internal space of the radiation unit, so as to be insertable into the internal space and held in an electrically insulating manner in respect of the radiation unit by spacer elements. The outer electrically conductive surface is connectible to an electrical voltage supply in order to detect if the outer surface of the collision detecting unit abuts against the inside surface of the radiation unit. The invention also relates to a method for performing such collision detection.

13 Claims, 2 Drawing Sheets

COLLISION DETECTING DEVICE AND METHOD

This is a 35 U.S.C. §371 filing of International Patent Application No. PCT/SE2005/000991, filed Jun. 23, 2005, which claims the benefit under 35 U.S.C. §119 (a)-(d) of Swedish Application No. 0401695-2, filed Jul. 1, 2004, and under 35 U.S.C.§119 (e) of U.S. Provisional Patent Application No. 60/583,361, filed Jun. 29, 2004.

TECHNICAL FIELD

The present invention relates to a collision detecting device for a radiation treatment apparatus, comprising a radiation unit having an internal space, for directing radiation beams towards a radiological focus in the internal space for treatment of a target in a patient's body therein. More precisely the collision detecting device functions to detect whether the body part or any equipment connected thereto, comes in contact with surfaces defining the internal space of the radiation unit when moving the patient inside the space to position the target to be treated in the radiological focus.

The invention also relates to a method for performing such collision detection.

BACKGROUND OF THE INVENTION

The invention relates primarily to so called radiation surgery where radiation beams, typically gamma radiation, are focused towards a limited area, a so called radiological focus, inside tissue. Through the focusing of the radiation beams, a high radiation dose can be achieved in the radiological focus such that the tissue in this focus area can be destroyed. In this way it is possible to destroy for example cancerous tumors inside the brain without having to open the skull.

However, the invention is applicable to any radiation treatment where some kind of focusing of the radiation beams are involved, for example radiation therapy where the main purpose is not to destroy the tissue immediately but through repeatedly treatments gradually deplete the affected tissue. The invention also relates to radiation surgery or therapy of other parts of the body than the brain, though the brain is particularly well suited for this kind of treatment, since it is fixedly positioned in relation to the skull which makes it possible to perform the treatment with high precision. The organs in for example the trunk, on the contrary, are more movable in relation to the skeleton, which makes it more difficult to perform this kind of radiation treatment with high precision. Fixation of affected tissue in relation to treatment equipment is more simple in for example an arm, a leg or in the vicinity of the spinal column where it is possible to secure the tissue in relation to the equipment via the bones.

Consequently, the invention is applicable to all radiation treatment where some form of focusing of the radiation beams is involved. Under these circumstances arises often a need for displacement of the patient or the body part within the treatment volume inside the radiation unit to position the target area to be treated in the radiological focus. The radiation unit may have many different shapes and normally has the form of a bowl or sphere with a treatment volume formed like a cavity, or a ring having a circular, square or other form where the treatment volume merely takes the form of a through bore. The body part to be treated is consequently inserted into the treatment volume and displaced until the target area to be treated is in the radiological focus. During the treatment process it might even be necessary to displace the body part to achieve a regular and comprehensive radiation of the hole affected area. During this displacement of the body part, it is always a risk that the body part or any equipment connected thereto, e.g. a fixation device for fixation of the body part, will collide with the interior of the radiation unit with a risk for injury of the patient or damage of the equipment as a consequence.

For example when radiation surgery is performed on a brain, the skull is secured to a fixation frame, a so called stereotactic frame, by means of fixation pins which are threaded into the skull of the patient. The stereotactic frame is in turn secured to a displacement device in the radiation device during diagnosis and treatment. In this way the brain can be positioned in a coordinate reference system and the travel path during treatment can be calculated in advance with great accuracy. The displacement during treatment is normally performed automatically by means of electrical motors, on the one hand because of avoiding exposing the medical personnel for excessive radiation, but also to be able to carry out the treatment with sufficient accuracy in terms of travel path as well as travel rate and dwell time.

In the prior art it is known to detect possible collision by measuring the power supplied to the motors. When the power feed exceeds a predetermined value, the power feed is interrupted and the motors stops accordingly. One problem with such a solution is that the power supply break point can not be set to low because this could lead to an inadvertent interruption due to a natural interference or a heavy patient/body part. Setting the break point to high, on the other hand, could lead to damage of equipment, dislocation of the body part in respect of the coordinate reference system, or even to injury of the patient, in case of a collision. When performing radiation surgery of the brain, it is possible not only to displace the head of the patient during treatment, but at the same time displace the hole body of the patient in order to avoid tensions in the equipment as well as to avoid discomfort for the patient. When displacing the entire body, a considerably larger force is required than when displacing only a part of the body, e.g. the head. Consequently, the break point must be set correspondingly higher which, in case of a collision, will lead to more serious damage until the motors stops.

SUMMARY OF THE INVENTION

It is an object of the present invention to eliminate the drawbacks and disadvantages of the prior art and provide a collision detecting device capable of detecting any collision between a radiation treatment unit and a patient/body part or any equipment attached thereto, which is reliable as well as simple to manufacture, install and use and hence inexpensive. At least this object is achieved by a collision detecting device according to the present invention.

The invention also relates to a method for performing such collision detection with essentially the same object as above. This is achieved by a method according to the present invention.

The invention is based on the understanding that a reliable collision detection may be accomplished by providing the radiation unit internally with a collision detecting unit, which at least on its exterior surface comprises an electrical conductive layer, and which is held separated a small distance from the radiation unit by electrical insulating spacer elements. After installation, the collision detecting unit is connected to a voltage supply. By monitoring the voltage level in the collision detecting unit, any collision between a body part of the patient or any equipment attached thereto and the inside of the radiation unit, may then be readily detected since, in such case, the walls of the collision detecting unit will be deformed or displaced such that the conductive layer will come into contact with the radiation unit and accordingly grounded, resulting in a drop of the voltage level to 0 Volt.

The monitoring may be performed in different ways. The simplest way is to display the voltage at the collision detecting unit on a gauge indicator for manually reading of an operator, or let the voltage drop activate some kind of visual or audible alarm device. The operator may then interrupt the displacement of the patient if a collision is detected. However, it is preferred that the monitoring is carried out automatically, by some kind of a monitoring device, such that the equipment moving the patient is stopped, e.g. by interrupting the power supply to the motors performing the movement.

The collision detecting unit may be manufactured in different ways and of various materials. In one embodiment the collision detecting unit is made of an electrically insulating material, e.g. plastics which preferably can be extruded or injection moulded into the desired shape. Subsequently the collision detecting unit is provided with an electrically conducting layer on the outside, e.g. an electrically conducting paint or a metal foil. In this way the inside of the collision detecting unit will be electrically insulated, which will protect the patient from electrical shocks in case of a collision.

In a further embodiment the body of the collision detecting unit instead is made of an electrically conducting material, preferably metal, and subsequently the inside preferably is covered with an electrically insulating material, e.g. paint or plastics. Certainly, it is possible to manufacture the collision detecting unit of an electrically conductive material without any electrically insulating layer on the inside, since the voltage level will be low enough, e.g. below 15 V, so that it will be harmless to the patient, but nevertheless it may feel unpleasantly.

Whether making the body of the collision detecting unit of an electrically insulating or an electrically conductive material, the body can either be made thin and flexible, such that electrical contact is achieved by flexing of the walls of the body in case of a collision, or the body can be made rigid, such that electrical contact is achieved by displacement of the entire body in case of a collision. In the former case, the spacer elements may be of a rigid material, such as tape strips or plastic knobs. In the latter case, the spacer elements must be elastic themselves or be held in an elastic way, such as spacer elements of rubber, foam rubber or springs, or plastic knobs held by springs. It is also necessary to provide the spacer elements in a recess in the collision detecting unit or the radiation unit. One advantage of having elastic or elastically hold spacer elements, is that it then is possible to detect a collision even in the vicinity of a spacer element. One requirement for the collision detecting unit to function, is that the collision detecting unit is held in an electrically insulating way in relation to the radiation unit. This doesn't necessarily imply that the spacer element itself has to be of an electrically insulating material, but it has to be held in an electrically insulating way, such for example a metallic spring bearing against an insulating seating on the collision detecting unit.

Also the shape of the collision detecting unit can vary in dependence of the shape of the internal space of the radiation unit, because it is desirable that the gap between the collision detecting unit and the radiation unit, will be sufficiently small. Consequently, the collision detecting unit may be formed e.g. as a ring or a cylinder with a through bore, or as a bowl being closed in one end. It may also have varying cross-sectional dimensions along its length.

The form and material of the spacer elements is optional. The main requirement is that they should be able to hold the collision detecting unit securely in an electrically insulating way on a small distance from the interior surfaces of the radiation unit. In one embodiment the spacer elements are strips of tape fastened to the outside of the collision detecting unit. Such spacer elements are inexpensive as well as easily and quickly fastened wherever it is suitable, and are able to hold the collision detecting unit at a very short distance from the interior surface of the radiation unit. However, it is possible to manufacture the spacer elements of other materials and with different shapes, such as elastic spacer elements as mentioned hereinbefore. It also would be possible to form the spacer elements simultaneously as injection moulding of the plastic body to the collision detecting unit, and consequently of the same material as and integral with the plastic body.

Since the collision detecting unit, in case of a rigid spacer element can not be deformed at the location of each spacer element, and consequently not detect any collision there, it is most appropriate to position such spacer elements where the probability for a collision is least. When treatment of a head, these positions usually are straight ahead, behind and to each side in relation to the head. This is due to the fact that normally fixation pins of a stereotactic frame are attached "diagonally" in respect of these locations and, since the fixation pins normally protrudes a distance from the head, the probability is large that any of the fixation pins will impinge against the collision detecting unit even if the head is moved straight forward, rearward or to the sides.

In a preferred embodiment, the collision detecting unit is connected to the voltage supply as well as the gauge indicator or the monitoring device, through one or more spring-loaded touch probes, which abuts against the electrically conducting layer on the outside of the collision detecting unit and transmits voltage to and/or from the same. A detachable touch probe of this kind makes the collision detecting unit easy to install and detach. However, it should be understood that the electrical connection also could be e.g. a fixed connection which consists of for example a wire soldered to the collision detecting unit.

In one embodiment, the collision detecting device according to the invention, is provided with only one touch probe, i.e. one single probe connects the collision detecting unit to the voltage supply as well as to the gauge indicator or the monitoring equipment. In another embodiment there are provided two separate touch probes, one for transmitting voltage to the collision detecting unit, and another for monitoring voltage level in the collision detecting unit. In this way the probability that a collision could occur, without it being detected, in consequence of a single touch probe being out of contact, is eliminated. With two separate touch probes, the gauge indicator or monitoring equipment is detecting collision if one of the touch probes is out of contact, which gives the operating personnel an opportunity to check the equipment before operation.

In an alternative embodiment, the collision detecting unit can be provided with electrically separated sectors in the outside conductive layer, each connected by one or two separate connecting means as described above. With such an arrangement it is possible to get an indication in what sector of the radiation unit a possible collision has occurred and to control an automatic displacement device to avoid the collision.

DETAILED DESCRIPTION OF PREFERRED EMBODIMENTS

Figure 1:
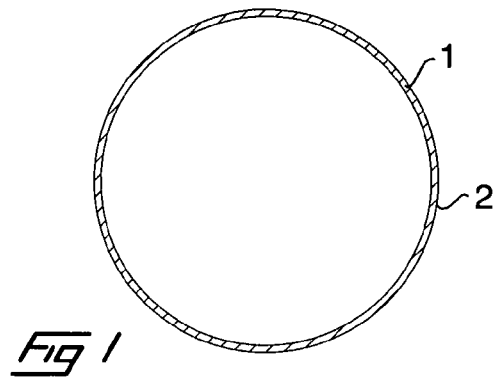
FIG. 1 is a cross section of a collision detecting unit according to a preferred embodiment of the present invention.
Figure 2:
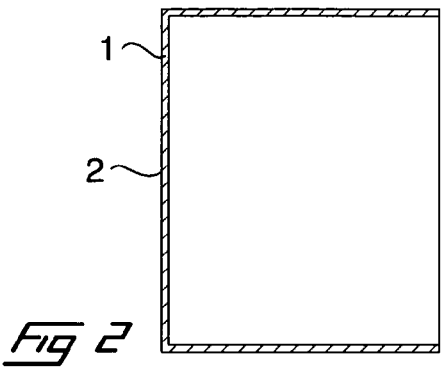
FIG. 2 is a longitudinal section through the collision detecting unit in FIG. 1.

In FIGS. 1 and 2 is shown an embodiment of a collision detecting unit 1 according to the invention. The shape of the collision detecting unit is determined by the shape of an internal space of a radiation unit to be inserted in. For the sake of simplicity the collision detecting unit is depicted as a simple cylindrical bowl, having a circular cross-section and one end closed. However, in practice the collision detecting unit may have a more intricate shape.

The collision detecting unit is preferably made of plastics, e.g. by injection moulding or any other suitable manufacturing method, and has thin, flexible walls which may easily deflect when subjected to a force.

Accordingly, the body of the collision detecting unit is electrically insulating. In accordance with the invention, however, the outer surfaces of the collision detecting unit, is provided with an electrically conductive layer 2, preferably of an electrically conductive paint, but other types of layers may also be possible, such as a thin metal foil.

Figure 3:
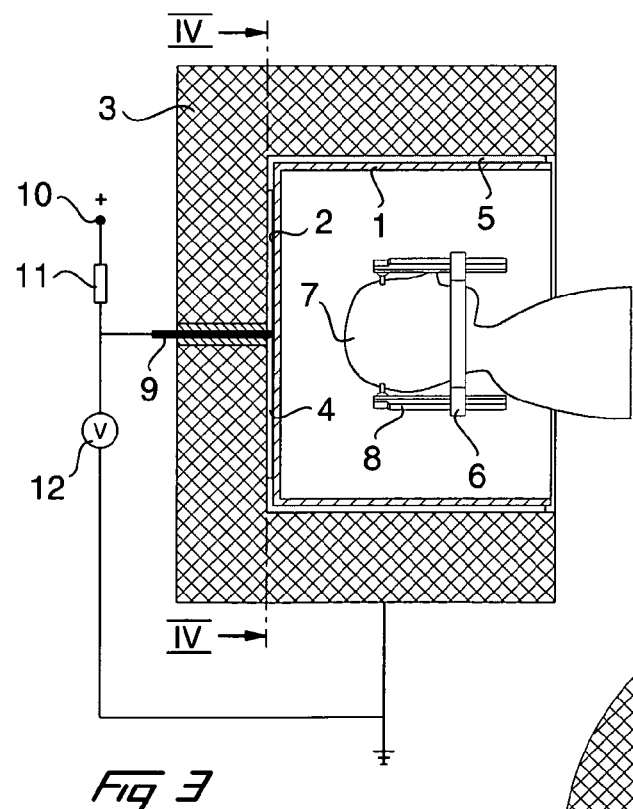
FIG. 3 is a schematic longitudinal section through an assembled radiation unit and collision detecting unit according to the invention, with the voltage feeding and monitoring device indicated.
Figure 4:
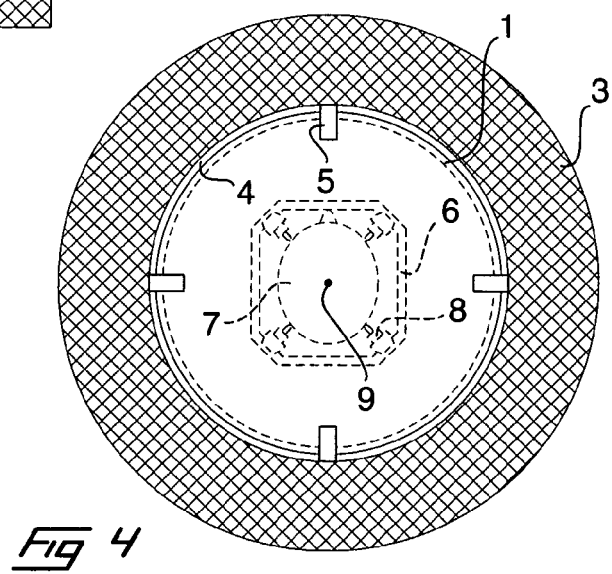
FIG. 4 is a cross section along the line IV-IV in FIG. 3.

In FIGS. 3 and 4 the collision detecting unit 1 is shown inserted in a schematic illustrated radiation unit 3. To prevent the outer electrically conducting layer of the collision detecting unit from coming into contact with the interior surfaces of the radiation unit, and form a small gap 4 between the collision detecting unit and the radiation unit, spacer elements in form of four elongate tape strips 5, are mounted between the collision detecting unit and the radiation unit in the preferred embodiment. However, the number of tape strips are optional and more or fewer tape strips are conceivable within the scope of the invention. The tape strips are extended on the outside and in the axial direction, over substantially the entire length of the collision detecting unit and a short distance over the end surface, as is best seen in FIG. 3. To as far as possible avoid that the spacer elements obstruct the detection of a collision, the tape strips are located in the positions uppermost, lowermost as well as furthest to each side. This may vary in dependence of the specific application, but for the application illustrated herein, a stereotactic frame 6 for fixation of a patient's head 7, has fixation pins 8 positioned "diagonally" in relation to the head. Accordingly it is most likely that the stereotactic frame, in the regions of one of the fixation pins, will impinge first on the collision detecting unit, which probably, as apparent from FIG. 4, will not be in the region of one of the spacer elements.

Also schematic shown in FIG. 3, is a combined voltage feeding and monitoring device, which is connected, through one single spring-loaded touch probe 9, to the electrically conducting layer 2 on the collision detecting unit 1. The voltage is conducted from a voltage supply 10 through an appropriate resistor 11 to the electrically conducting layer. A monitoring device 12 is here illustrated as a simple voltage gauge indicator, connected between the touch probe and earth, but it should be understood that it could also be a monitoring device adapted to emit signals to a control unit for automatic displacing of the patient inside the treatment space, or for interrupting the power supply to the motors performing the displacement when a collision is detected.

When a collision occurs, the stereotactic frame 6 or the patient will press against the collision detecting unit 1, which will deflect and the outer electrically conducting layer 2 comes to bear against the interior surface of the radiation unit. The voltage level in the collision detecting unit will thus drop to the same level as the radiation unit, which normally is 0 Volt since the radiation unit is grounded. This voltage drop can be read by the operator on the gauge indicator or sensed by the monitoring device 12.

Figure 5:
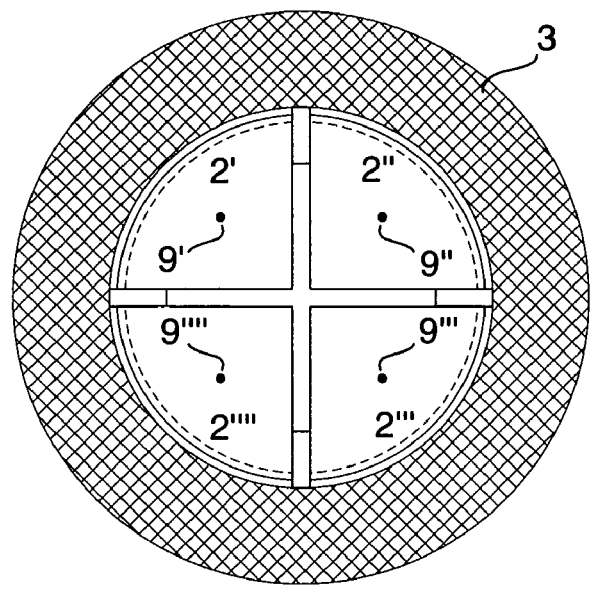
FIG. 5 is a cross section similar to FIG. 4 of an alternative embodiment.

In FIG. 5 is shown an alternative embodiment of the collision detecting unit according to the present invention. In this embodiment the electrically conductive layer on the outside of the collision detecting unit is divided into four separate sectors 2'-2'''', which are electrically insulated from each other. Each sector is separately connected to the voltage supply and the monitoring device, preferably through one or two touch probes 9'-9'''', as described above, which in the drawing are shown as dots. A collision detecting device constructed in this way makes it possible to detect in which sector a possible collision has occurred. Such information is very useful, for example for an automatic safety system, which can use the information to move the patient in correct direction after a collision has been detected.

Figure 6:
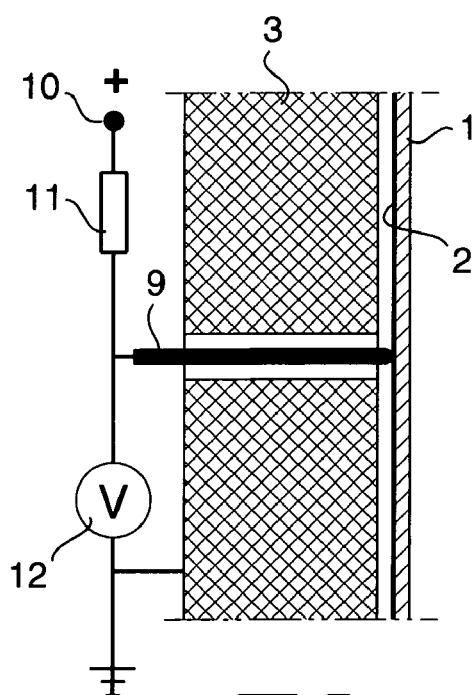
FIG. 6 is a schematic illustration of the voltage feeding and monitoring device in larger scale.
Figure 7:
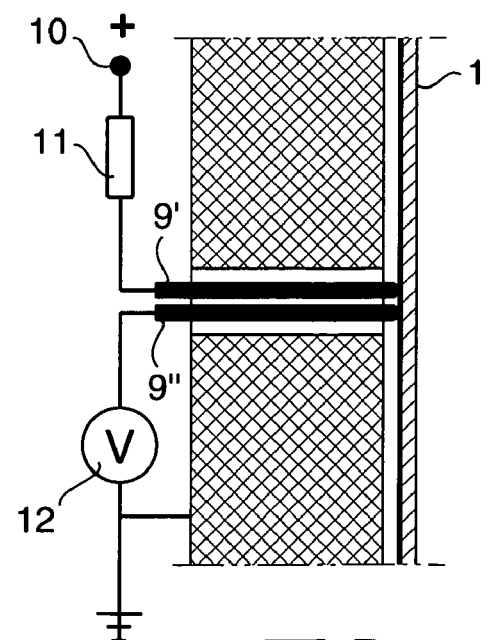
FIG. 7 is a schematic illustration of an alternative embodiment of the voltage feeding and monitoring device.

FIGS. 6 and 7 are schematic cross sections in enlarged scale, of two different embodiments of the electric connection of the collision detecting unit to the voltage supply and the monitoring device. In FIG. 6 the connection of the collision detecting unit 1 is achieved through one common touch probe 9, which connects the collision detecting unit with both the voltage supply 10 as well as the monitoring device 12. The touch probe is inserted through a hole in the radiation unit and is electrically insulated therefrom by an insulating insert. Preferably the touch probe is spring loaded (not shown) and abuts against the outer, electrically conducting layer 2 of the collision detecting unit through a contact pressure to ensure reliably electric contact. The touch probe 9 is connected to the voltage supply 10 via a resistor 11. A monitoring device 12, here depicted as a voltage gauge indicator, having a large internal resistance, is connected between the touch probe and ground. Also the radiation unit 3 is connected to ground. Normally, the collision detecting unit has a voltage level which is different from the voltage level in the radiation unit which is at 0 Volt. This is indicated by the monitoring device 12. However, when a collision occurs so that the electrically conducting layer 2 of the collision detecting unit 1 comes into contact with the radiation unit 3, the collision detecting unit will be short circuited to ground via the radiation unit, which is indicated by the monitoring device 12 to the operator or a control circuit. The resistor 11 prevents the voltage source 10 from being short circuited to ground at a collision.

However, if there should be an interrupted contact between the touch probe 9 and the collision detecting unit 1, in an electric circuit of the type described, the monitoring device 12 will indicate no collision even if there should be a collision. This problem is avoided by an electric circuit depicted in FIG. 7. Here the collision detecting unit, or each sector of the same, is connected by two touch probes 9', 9" which are electrically separated from each other. One of the touch probes connects the collision detecting unit 1 with the voltage supply 10 via a resistor 11, while the other connects the collision detecting unit with the monitoring device 12. If one or both of the touch probes should have no contact with the collision detecting unit, the monitoring device will measure 0 Volt on the collision detecting device, which indicates a possible collision. Consequently, the operator will have an opportunity to check equipment and take care of any problems.

The invention claimed is:

1. A collision detecting device for a radiation treatment apparatus, comprising a radiation unit having an internal space for directing radiation beams towards a radiological focus in the internal space for treatment of a target in a patient's body therein, wherein the collision detecting device functions to detect whether any body part or any equipment comes into contact with surfaces defining the internal space of the radiation unit when moving the patient inside the space to position the target to be treated in the radiological focus, wherein the collision detecting device comprises a collision detecting unit being electrically conductive at least on its outer surface and having a size smaller than the internal space of the radiation unit, so as to be insertable into the internal space and held in an electrically insulating manner in respect of the radiation unit so that its outer electrically conductive surface is held at a distance from the inner surface of the radiation unit, and being connected to an electrical voltage supply in order to detect if the outer surface of the collision detecting unit abuts against the inside surface of the radiation unit due to deformation or displacement of the collision detecting unit caused by the body part or any equipment attached thereto.

2. The collision detecting device according to claim 1, wherein the collision detecting unit is held at a distance from the inner surface of the radiation unit by spacer elements.

3. The collision detecting device according to claim 2, wherein the spacer elements are of an elastic material.

4. The collision detecting device according to claim 1, wherein the collision detecting unit is electrically insulated on its interior surface.

5. The collision detecting device according to claim 4, wherein the collision detecting unit is made of an electrically insulating material having an electrically conductive layer on its outer surface.

6. The collision detecting device according to claim 4, wherein the collision detecting unit is made of an electrically conductive material having an electrically insulating layer on its interior surface.

7. The collision detecting device according to claim 5, wherein the electrically conductive layer on the outer surface is divided into two or more separate sectors, which are electrically insulated from each other and each separately connected to a voltage supply and a monitoring device to enable detection of in which sector a possible collision has occurred.

8. The collision detecting device according to claim 5, wherein the collision detecting unit is painted with an electrically conductive paint on its outer surface.

9. The collision detecting device according to claim 6, wherein the collision detecting unit is painted with an electrically insulating paint on its interior surface.

10. The collision detecting device according to claim 1, wherein the outer surface of the collision detecting unit is electrically connected by a spring loaded touch probe.

11. The collision detecting device according to claim 10 in association with a monitoring device, wherein the collision detecting unit is connected by means of two separate touch probes, one for connection to the voltage supply and one for connection to the monitoring device.

12. The collision detecting device according to claim 1, wherein the collision detecting unit is connected to an automatic monitoring device, which senses and automatically interrupts the displacement of the patient by means of a device for automatic displacement.

13. Method for detecting collision between a part of a patient's body or any equipment attached thereto, and an inner surface of an internal space of a radiation unit when performing radiation treatment by means of a radiation treatment apparatus, comprising the steps of;
   providing a collision detecting unit being electrically conductive at least on its outer surface and having a size smaller than the internal space of the radiation unit;
   inserting the collision detecting unit into the internal space of the radiation unit in an electrically insulating manner in respect of the radiation unit, such that the outer electrically conductive surface of the collision detecting unit is held at a distance from the inner surface of the radiation unit;
   connecting the electrically conductive outer surface of the collision detecting unit to a voltage supply; and
   detecting possible collision between the body part or any equipment attached thereto, and the inside of the radiation unit, by monitoring any change of the voltage level in the collision detecting unit due to deformation or displacement of the collision detecting unit, caused by the body part or any equipment attached thereto, resulting in abutment against the radiation unit.

* * * * *